(12) United States Patent
Brosig et al.

(10) Patent No.: US 7,455,146 B2
(45) Date of Patent: Nov. 25, 2008

(54) METHOD AND DEVICE FOR RECOGNIZING THE LEVEL OF AWARENESS OF A VEHICLE DRIVER

(76) Inventors: Stefan Brosig, Kuckucksweg 6, Hankenbüttel (DE) 29386; Andreas Apel, Hinter den Höfen 47, Salzgitter (DE) 38228

( * ) Notice: Subject to any disclaimer, the term of this patent is extended or adjusted under 35 U.S.C. 154(b) by 332 days.

(21) Appl. No.: 10/524,351

(22) PCT Filed: Aug. 22, 2003

(86) PCT No.: PCT/EP03/09357
§ 371 (c)(1),
(2), (4) Date: Aug. 9, 2005

(87) PCT Pub. No.: WO2004/022376
PCT Pub. Date: Mar. 18, 2004

(65) Prior Publication Data
US 2007/0084661 A1   Apr. 19, 2007

(30) Foreign Application Priority Data
Sep. 4, 2002   (DE) .............................. 102 41 624

(51) Int. Cl.
*B60K 28/00* (2006.01)
(52) U.S. Cl. .................................................. 180/272
(58) Field of Classification Search ................. 180/272, 180/277, 280, 271; 280/735
See application file for complete search history.

(56) References Cited

U.S. PATENT DOCUMENTS

| | | | |
|---|---|---|---|
| 4,463,347 A * | 7/1984 | Seko et al. | 340/576 |
| 4,564,833 A * | 1/1986 | Seko et al. | 340/576 |
| 4,565,997 A * | 1/1986 | Seko et al. | 340/576 |
| 5,745,031 A | 4/1998 | Yamamoto | 340/439 |
| 5,769,085 A | 6/1998 | Kawakami et al. | 128/706 |

FOREIGN PATENT DOCUMENTS

| | | |
|---|---|---|
| DE | 4400207 | 7/1994 |
| DE | 195 15 429 C2 | 12/1995 |
| JP | 5262162 | 10/1993 |
| JP | 8202998 | 8/1996 |
| JP | 11263143 | 9/1999 |
| JP | 11339199 | 12/1999 |
| JP | 2000 193545 | 7/2000 |
| WO | WO 02/17787 | 3/2002 |

* cited by examiner

*Primary Examiner*—Faye M. Fleming
(74) *Attorney, Agent, or Firm*—Norris, McLaughlin & Marcus

(57) ABSTRACT

The invention relates to a method for detecting the attention level of a vehicle operator, wherein a steering performance of the vehicle operator is monitored, as well as to a device (30) for detecting the attention level of a vehicle operator, with at least one sensor device detecting the steering performance of the vehicle and with a signal measurement and evaluation unit (32).

Figure 1:
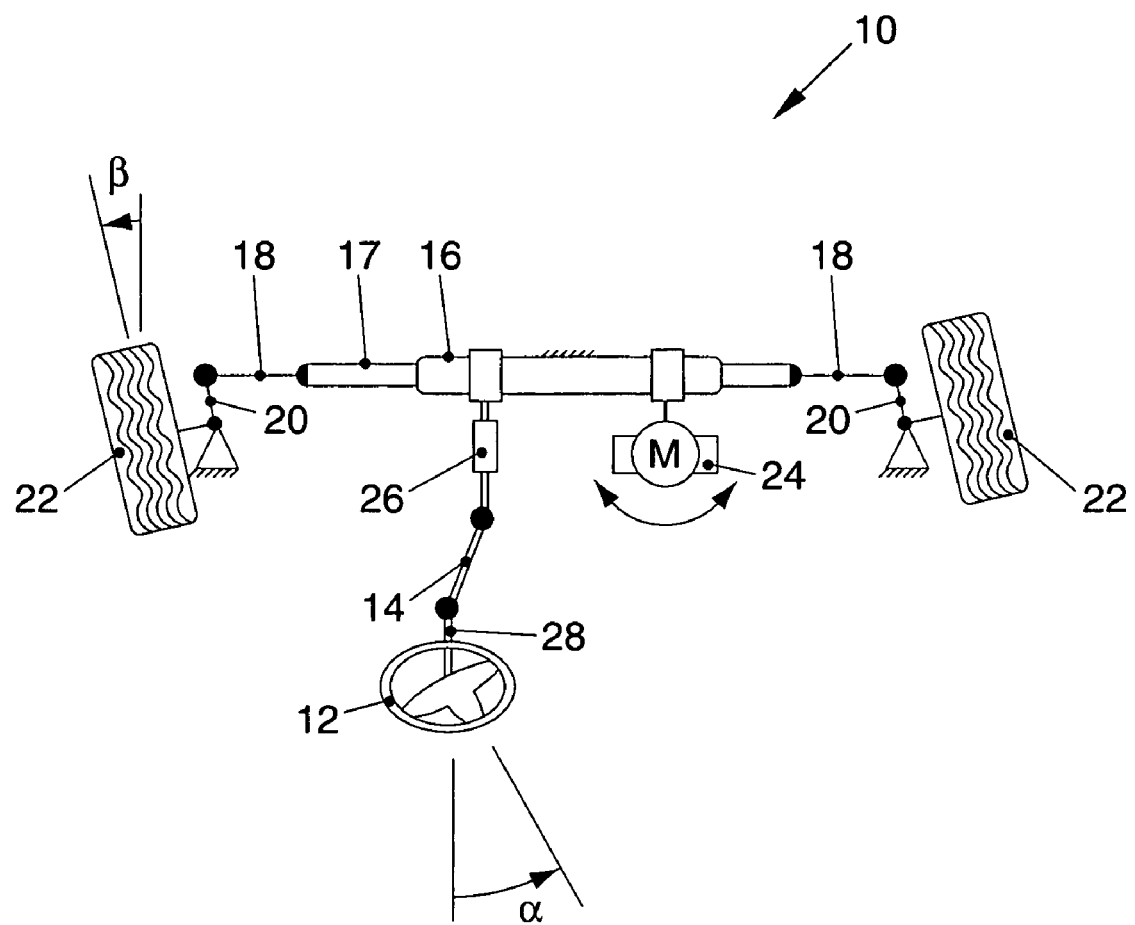

According to the method of the invention, a phase relationship between a change of a steering angle ($\beta$) of at least one steerable wheel (22) of the vehicle and a change of the steering wheel angle ($\alpha$) is evaluated. With the device of the invention, at least one signal (48) corresponding to the attention level can be generated, with the signal depending on a phase relationship between a steering angle ($\beta$) of at least one steerable wheel (22) of the vehicle and a steering wheel angle ($\alpha$).

16 Claims, 3 Drawing Sheets

METHOD AND DEVICE FOR RECOGNIZING THE LEVEL OF AWARENESS OF A VEHICLE DRIVER

This application is a 371 of PCT/EP03/09357, filed Aug. 22, 2003.

The invention is directed to a method and a device for detecting the attention level of a vehicle operator by monitoring a steering performance of the vehicle operator, with the features recited in the preambles of claims 1 and 15.

It is generally known that particularly high demands are placed on the attention level (vigilance) of vehicle operators. A decreased attention level of the vehicle operator, in particular due to fatigue and/or a monotonous driving situation, can increase the likelihood of an accident.

Methods and devices for improving the attention level of a vehicle operator are known. For example, DE 44 00 207 C2 discloses a device and a method that correlates heartbeat information of the vehicle operator with steering information. Actuation of the steering wheel by the vehicle operator is detected with at least one steering angle sensor. Specific time periods before the vehicle operator turns the steering wheel clockwise or counterclockwise are monitored to detect actuation of the steering wheel by the vehicle operator. The underlying concept is here that the operator tends to maintain the course of the vehicle with so-called fine-steering periods that occur more frequently when the vehicle operator is alert. An absence of these fine-steering-periods or a greater time interval between these fine-steering-periods could indicate a reduced attention level of the vehicle operator.

It is generally known that steering performance of a vehicle can be affected either intentionally by the operator or by external effects, such as wind gusts, poor road conditions and the like, which require course corrections from the vehicle operator.

It is also known to equip vehicles with electronic stabilizer systems (ESP) and/or an electric steering assist (EPS). With these systems, an active control system detects deviations between the desired performance and the actual performance of various components and automatically initiates suitable countermeasures, thereby aiding the vehicle operator in steering the vehicle.

It is therefore an object of the invention to provide a method and a device of the aforedescribed type for readily detecting the attention level of a vehicle operator.

According to the invention, the object is solved by a method with the features recited in claim 1. The attention level of a vehicle operator can be easily and reliably determined by evaluating a phase relationship between a change of a steering angle of at least one steerable wheel of a vehicle and a change of a steering wheel angle. The method of the invention is based on the observation that the vehicle operator must initiate a counter-steering action to correct the desired vehicle course when an external event affects steering of the vehicle. The external effect on the vehicle course causes a change in the steering angle of at least one steerable wheel of the vehicle, i.e., the actual steering angle deviates from the intended steering angle. The vehicle operator uses the steering wheel to counter-steer, so that the change in the steering wheel angle is a measure for the steering action of the vehicle operator. Due to inevitable reaction times, the phase relationship between the steering angle of the at least one steerable wheel and the steering wheel angle can be different. This difference between the phase relationship of the steering angle and the steering wheel angle is therefore a measure of the ability of the vehicle operator to react (reaction speed), so that a diminishing reaction speed can readily indicate a reduced attention level of the vehicle operator.

According to an advantageous feature of the invention, the phase relationship can be evaluated during time intervals when steering movements of the vehicle are not caused by an intentional steering action of the vehicle operator. This significantly reduces the complexity for identifying the attention level of the vehicle operator. The method for identifying the attention level according to the invention is applied only after external steering effects cause a steering action of the vehicle. Conversely, the method of the invention is preferably inactive during time intervals when the vehicle operator initiates a steering action or the steering action is not influenced by an external event.

According to another advantageous feature of the invention, the phase relationship can be evaluated within a time interval where the change of the steering wheel angle follows a change of the steering angle. Preferably, the length of the time interval and/or a slope of the steering angle during that time interval can be evaluated, preferably within predefinable time windows. In this way, different evaluation modes can advantageously be selected that can optionally be executed successively.

According to yet another feature of the invention, the length of the time interval and/or the slope can be compared with at least one predefinable limit value, wherein advantageously a frequency is monitored by which the at least one limit value is exceeded during a predefinable time interval. This makes it possible to easily detect the attention level, in particular its change over time.

Moreover, according to an advantageous feature of the invention, at least one action can be initiated when the at least one limit value is reached within a predefinable tolerance limit, when the at least one limit value is exceeded and/or when the at least one limit value is exceeded with a frequency greater than a predefined frequency. The action can specifically include an automatic steering intervention, an/or generation of at least one acoustic, optic and/or haptic message. The vehicle operator can thereby be alerted of a drop in his/her attention level, or the decrease in the attention level can be automatically compensated, which effectively reduces the probability for an accident due to the decreasing attention level of the vehicle operator. Optionally, stepped actions can be initiated depending on a detected attention level, in particular depending on the severity of a detected decrease in the attention level. In this way, the intensity of warning messages can be correlated with the decreasing attention level of the vehicle operator, such as giving the vehicle operator timely warnings, for example, to interrupt the trip for a brief rest and the like.

According to yet another advantageous feature of the invention, the steering angle and the steering wheel angle can be determined by evaluating an angular position and/or a rotation speed of the rotor of a servo motor of the electric steering assist and an angular position of a steering column. These signals are already available in vehicles equipped with an electric steering support (EPS) for other measurement and control tasks, thus obviating the need to install additional sensors for measuring and evaluating the phase relationship between steering angle and steering wheel angle.

Advantageously, the phase difference can be determined by evaluating a steering torque of an electric steering assist, whereby existing sensors and/or their measured values can advantageously be used indirectly. The signal corresponding to the steering torque depends on the difference between the steering angle and the steering wheel angle, thereby providing a redundant signal for identifying the attention level.

Accordingly, a single signal can be used to evaluate phase differences, which significantly simplifies in the accuracy and the implementation of the method.

The object of the invention is also solved by a device with the features recited in claim 15. Advantageously, the device can be readily integrated in a vehicle by providing at least one sensor device that detects the steering performance of the vehicle and cooperates with a signal measurement and evaluation unit capable of generating a signal corresponding to the attention level, with the generated signal depending on a phase relationship between a steering angle of at least one steerable wheel of the vehicle and a steering wheel angle. In particular, the device can be part of a control device of the vehicle.

Additional advantageous embodiments of the invention are recited as additional features in the dependent claims.

Figure 2:
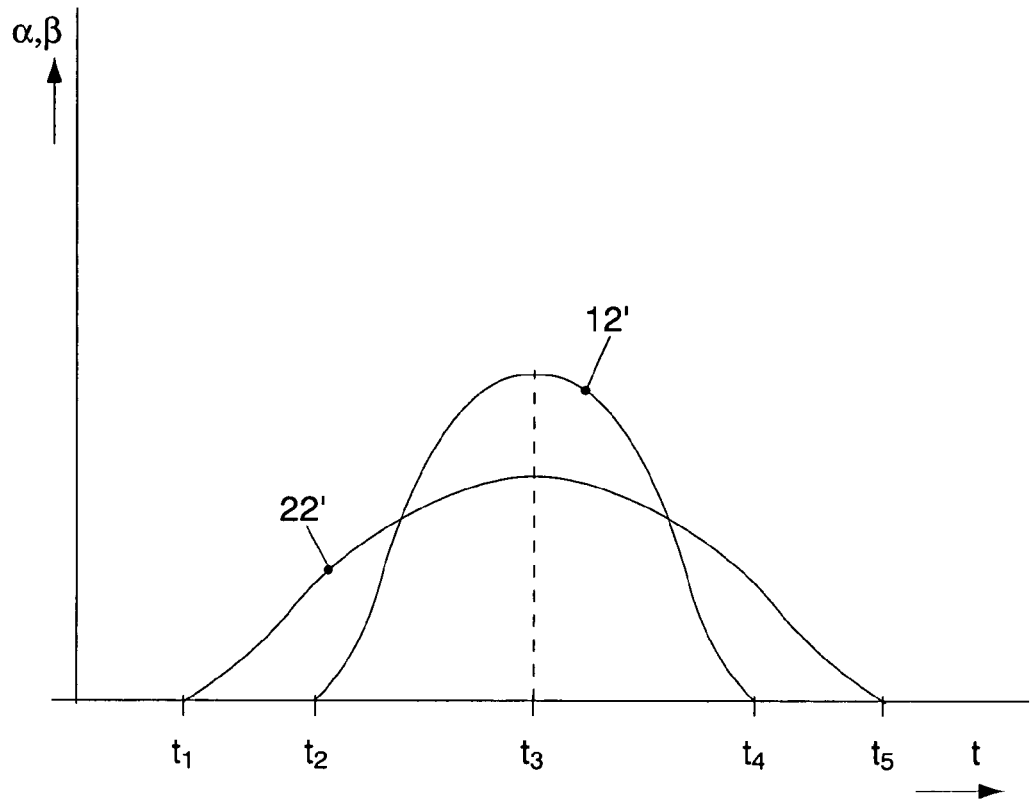
Figure 2A:
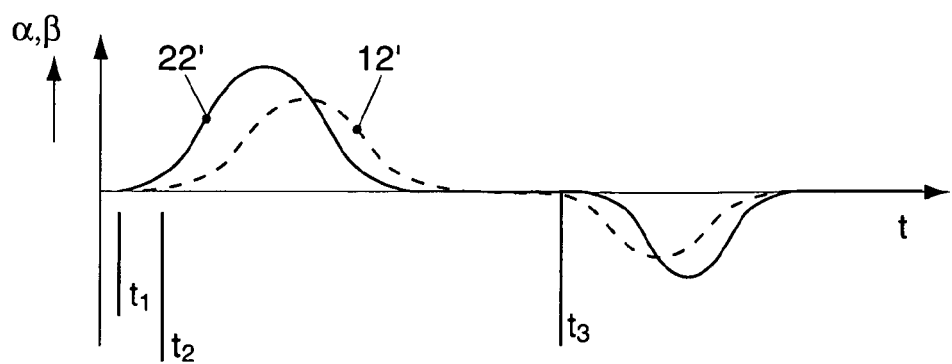
Figure 3:
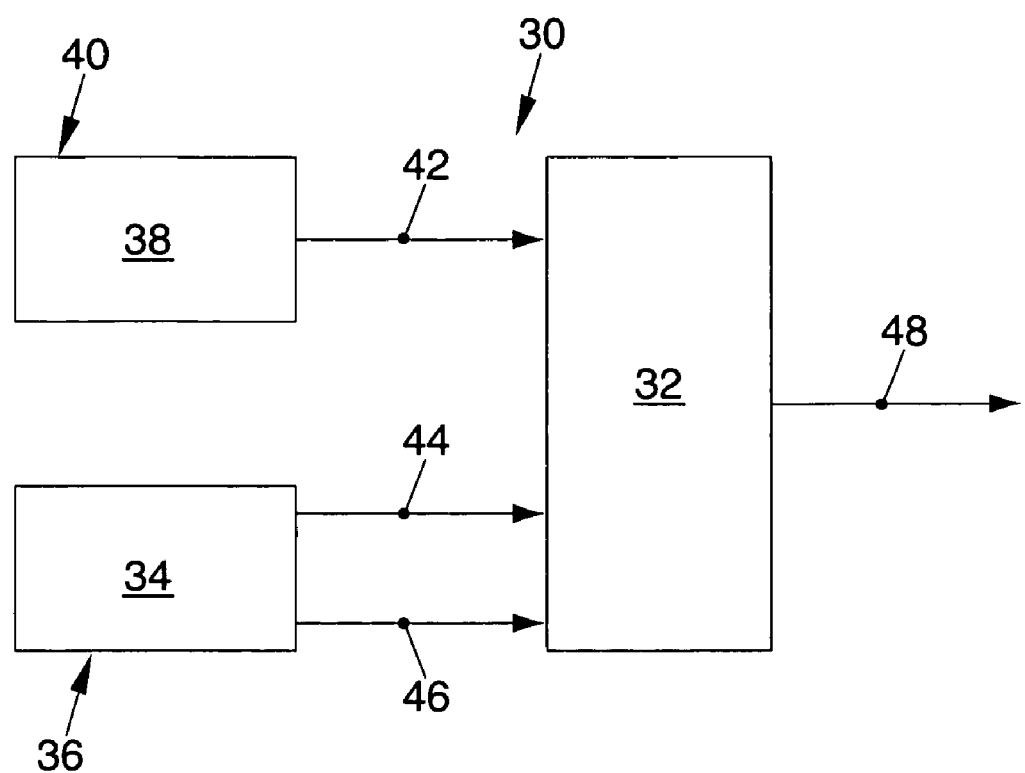

Embodiments of the invention will be described in detail hereinafter with reference to the appended drawings. It is shown in:

FIG. 1 a schematic diagram of a steering assembly of a vehicle;

FIGS. 2 and 2a characteristic curves of a steering angle and a steering wheel angle; and FIG. 3 a block diagram of a device for detecting the attention level.

FIG. 1 shows schematically a steering assembly 10 of an automobile. The steering assembly 10 includes a steering wheel 12 that is connected with a steering shaft 14 and operates on a steering rack 17 arranged in a steering box 16. The steering rack 17 is connected to tie rods 18 that operate on steering arms 20. The steering arms 20 support the steerable wheels 22 of the automobile, in particular the front wheels of the automobile. The steering assembly 10 includes an electric servo motor 24 that assists steering. A torsion rod 26 is integrated in the steering shaft 14. The steering shaft 14 is also provided with a steering angle sensor 28.

The design and the operation of the schematically depicted steering assembly 10 are generally known and will therefore not be discussed in detail in the context of the present specification.

It should be noted that when the steering assembly 10 is activated, a defined steering angle $\beta$ of the wheels 22 is associated with each steering wheel angle $\alpha$ of the steering wheel 12 by way of the active connection between the steering wheel 12 and the steerable wheels 22.

FIG. 2 shows in form of a curve 22' the time dependence of the steering angle $\beta$ and in form of a curve 12' the time dependence of the steering wheel angle $\alpha$ based on the method of the invention. It is important to note that the steering angle $\beta$ and the steering wheel angle $\alpha$ are not intentionally changed by the vehicle operator, but that these changes are caused by external effects, such as wind gusts, obstacles on the road, poor road conditions, poor tracking ability of the vehicle and the like.

These external effects have in common that initially the steering angle $\beta$ (curve 22') changes. As illustrated in FIG. 2, the steering angle $\beta$ changes at a time $t_1$ due to an external effect. Depending on the design, the change in the steering angle $\beta$ is followed at time $t_2$ by a change in the steering wheel angle $\alpha$, here shown as curve 12'. The time interval from $t_1$ to $t_2$ is determined by the steering mechanism, for example, by play in the steering assembly 10, by the response of the torsion rod 26 and the like. It is important to remember that the method of the invention is applied only when the change in the steering wheel angle $\alpha$ is caused by the change in the steering angle $\beta$. The vehicle operator detects the change in the steering angle $\beta$ and corrects the steering wheel angle $\alpha$ with a time delay $t_2-t_1$. Stated differently: ideally, at the time $t_2$, the vehicle operator notices that the steering angle $\beta$, i.e., the actual steering angle, differs from the desired steering angle $\beta$. This causes the vehicle operator to react by attempting to force the actual steering angle $\beta$ to coincide with the desired steering angle $\beta$. On a presumably straight course, the desired steering angle $\beta$ is 0°, while the desired steering wheel angle $\alpha$ is also 0°. The actual steering angle $\beta$ at time $t_1$ increases due to external effects, and the actual steering wheel angle $\alpha$ also increases with a time delay $t_2-t_1$.

At time $t_3$, the vehicle operator notices that the actual steering angle $\beta$ deviates from the desired steering angle $\beta$ and attempts to compensate by turning the steering wheel 12. The steering wheel angle $\alpha$ then decreases when the vehicle operator turns the steering wheel 12, with the steering angle $\beta$ also decreasing with a time delay that depends on the mechanical system. Accordingly, the steering wheel angle $\alpha$ at time $t_4$ again corresponds to the desired steering wheel angle $\alpha$, while the actual steering angle $\beta$ at time $t_5$ corresponds to the desired steering angle $\beta$.

Conclusions about the attention level of the vehicle operator can thus be drawn from the evolution of the time interval $t_3-t_2$. The more attentive the vehicle operator is, the earlier he/she will detect that the actual steering angle $\beta$ deviates from the desired steering angle $\beta$. In other words, the shorter the time interval $t_3-t_2$, the greater the attention level of the vehicle operator.

FIG. 2a shows an embodiment where the steering angle $\beta$ changes due to short and impulse-like disturbances. Accordingly, the steering wheel angle $\alpha$ is actively corrected only following the short and impulse-like disturbance. The vehicle operator only reacts at time $t_3$, i.e., after the short and impulse-like disturbance has already passed. However, the vehicle operator must react because such short and impulse-like disturbances can adversely affect the straight course of the vehicle. Accordingly, the time interval $t_3-t_2$ is also an indication of the attention level of the vehicle operator.

The evaluation can be performed as follows:

The time interval $t_3-t_2$ is measured and compared with a limit value. If the time interval $t_3-t_2$ exceeds the limit value, then a warning signal is generated commensurate with the attention level of the vehicle operator. The warning signal can include acoustic, optic or haptic information. If the time interval $t_3-t_2$ exceeds the limit value by a predefinable amount, then an automatic steering correction can also be applied, returning the actual steering angle $\beta$ to the desired steering angle $\beta$.

According to another feature of the evaluation method, the slope of the increase of the steering wheel angle $\alpha$ can be evaluated beginning at time $t_2$. If the slope of the steering wheel angle $\alpha$ is the greater than a predefinable slope, without detecting a reaction from the vehicle operator (time $t_3$), then a warning message can again be generated commensurate with the reduced attention level of the vehicle operator. An additional automatic steering correction can also be applied when a certain slope, i.e., predefinable limit value, is exceeded.

In another approach, a ratio is formed between the slope of the steering angle $\beta$ beginning at time $t_1$ and the slope of the steering wheel angle $\alpha$ beginning at time $t_2$. Based on the fact that a defined steering wheel angle $\alpha$ is associated with each defined steering angle $\beta$, a detected decrease in the slope of the steering wheel angle $\alpha$ would indicate that the vehicle operator has noticed a deviation of the actual steering angle $\beta$ from the desired steering angle $\beta$, prompting a suitable correction. Accordingly, this approach also provides an indication for the attention level of the vehicle operator.

According to another feature of the evaluation method, the frequency with which the time interval from $t_3$ to $t_2$ exceeds a predefinable limit value can also be used as a reference variable. The time interval between $t_3$ and $t_2$ defines the reaction time of the vehicle operator in response to external steering effects. If the frequency with which the time interval between $t_3$ and $t_2$ exceeds a limit value increases, albeit by a very small amount, then this could further indicate a decreasing attention level of the vehicle operator.

FIG. 3 shows in form of a block diagram a device 30 for identifying the attention level of a vehicle operator. The device 30 includes a signal measurement and evaluation unit 32 that is connected with a controller 34 of an electric steering assist (EPS) 36. The signal measurement and evaluation unit 32 can also be connected with a controller 38 of an electronic stabilizing system (ESP) 40. The signal measurement and evaluation unit 32 receives from the ESP system, for example, a signal 42 that corresponds to the actual steering angle $\beta$. The signal measurement and evaluation unit 32 can also receive from the EPS system 36 a signal 44 that corresponds to an angular position and/or a rotation speed of a rotor of the electric servo motor 24. A signal 46 that corresponds to an actual steering torque, measured by way of the torsion rod 26 can also be supplied. Accordingly, the signal measurement and evaluation unit 32 can use existing signals in vehicles equipped with the EPS system 36 and/or the ESP system 40. Additional sensor devices and the like are therefore not required for identifying the attention level of the vehicle operator according to the invention. The signal measurement and evaluation unit 32 generates a signal 48 that corresponds to the attention level of the vehicle operator and can be used to generate a corresponding action, for example a steering intervention or an acoustic, visual or haptic warning message. Moreover, the signal 48 can also initiate a stepped action commensurate with the attention level of the vehicle operator as detected by the aforedescribed evaluation, which can include, for example, initially an optical warning signal, followed by a combined optic and acoustic warning signal, and if necessary followed by an optic, acoustic and haptic warning signal. Finally, an automatic steering intervention can occur if the attention level of the vehicle operator is significantly impaired.

LIST OF REFERENCE CHARACTERS 10 steering assembly
12 steering wheel
12' characteristic curve (curve of steering wheel angle $\alpha$)
14 steering shaft
16 steering box
17 steering rack
18 tie rods
20 steering arms
22 wheels
22' characteristic curve (curve of wheel angle $\beta$)
24 servo motor
26 torsion rod
28 steering angle sensor
30 device for detecting the attention level
32 signal measurement and evaluation unit
34 controller for 36
36 electric steering assist (EPS system)
38 controller for 40
40 electronic stabilizing system (ESP system)
42 signal (corresponds to steering angle $\beta$)
44 signal (corresponds to angular position and/or rotation speed of a rotor of the electric servo motor 24)
46 signal (corresponds to the actual steering torque, measured via the torsion rod 26)
48 signal (corresponds to the attention of the vehicle operator)
$\alpha$ steering wheel angle
$\beta$ steering angle
$t_n$ points in time

The invention claimed is:

1. A method for detecting a level of awareness of a vehicle driver by monitoring a steering behavior of the vehicle driver and evaluating a phase profile between a change in a steering angle ($\beta$) of at least one steerable wheel of a vehicle and a change in a steering-wheel angle ($\alpha$) of a steering wheel of the vehicle, the method comprising:

Determining a first $t_1$, wherein the change in the steering angle ($\beta$) begins at the first time $t_1$;
determining a second time $t_2$, wherein the change in the steering-wheel angle ($\alpha$) begins at the second time $t_2$ and the second time $t_2$ follows the first time $t_1$;
determining a third time $t_3$, wherein the vehicle driver starts to bring about compensation by actuation of the steering wheel at the third time $t_3$; and
evaluating a gradient of the steering-wheel angle ($\alpha$) during a time interval from the second time $t_2$ to the third time $t_3$ for detecting the level of awareness of the vehicle driver.

2. A method for detecting the level of awareness of a vehicle driver by monitoring a steering behavior of the vehicle driver and evaluating a phase profile between a change in a steering angle ($\beta$) of at least one steerable wheel of a vehicle and a change in a steering-wheel angle ($\alpha$) of a steering wheel of the vehicle, the method comprising:

determining a first time $t_1$, wherein the change in the steering angle ($\beta$) begins at the first time $t_1$;
determining a second time $t_2$, wherein the change in the steering-wheel angle ($\alpha$) begins at the second time $t_2$ and the second time $t_2$ follows the first time $t_1$;
determining a third time $t_3$, wherein the vehicle driver starts to bring about compensation by actuation of the steering wheel at the third time $t_3$; and
comparing a gradient of the steering-wheel angle ($\alpha$) with a gradient of the steering angle ($\beta$) to detect the level of awareness of the vehicle driver.

3. The method according to claim 1, wherein the gradient of the steering-wheel angle ($\alpha$) is compared with at least one predefinable limiting value.

4. The method according to claim 1, wherein a frequency of exceeding of the at least one limiting value is monitored over a predefinable time interval.

5. The method according to claim 2, wherein a frequency of exceeding of the at least one limiting value is monitored over a predefinable time interval.

6. The method according to claim 3, further comprising:
triggering at least one action at a predefinable approximation to the at least one predefinable limiting value, at an exceeding of the at least one limiting value or at a frequency of exceeding of the at least one predefinable limiting value.

7. The method according to claim 6, wherein the at least one action is an automatic steering intervention.

8. The method according to claim 6, wherein the at least one action is at least one acoustic, visual or haptic indication.

9. The method according to claim 1, further comprising:
triggering at least one action which is graded as a function of a detected level of awareness.

10. The method according to claim 2, further comprising:
triggering at least one action which is graded as a function of a detected level of awareness.

11. The method according to claim 1, further comprising:

evaluating an angular position or a rotational speed of a rotor of a servomotor of an electric steering assistance means and an angular position of a steering column to determine the steering angle ($\beta$) and the steering-wheel angle ($\alpha$).

12. The method according to claim 2, further comprising:

evaluating an angular position or a rotational speed of a rotor of a servomotor of an electric steering assistance means and an angular position of a steering column to determine the steering angle ($\beta$) and the steering-wheel angle ($\alpha$).

13. The method according to claim 1, further comprising:

evaluating a steering torque of an electric steering assistance means to determine the change of the steering angle ($\beta$) and the steering-wheel angle ($\alpha$).

14. The method according to claim 2, further comprising:

evaluating a steering torque of an electric steering assistance means to determine the change of the steering angle ($\beta$) and the steering-wheel angle ($\alpha$).

15. An apparatus for detecting a level of awareness of a vehicle driver and a phase profile between a change in a steering angle ($\beta$) of at least one steerable wheel of a vehicle and a change in a steering-wheel angle ($\alpha$) of a steering wheel of the vehicle the apparatus comprising:

at least one sensing device which detects a steering behavior of a vehicle;

means for determining a first time $t_1$, wherein the change in the steering angle ($\beta$) begins at the first time $t_1$;

means for determining a second time $t_2$, wherein the change in the steering-wheel angle ($\alpha$) begins at the second time $t_2$ and the second time $t_2$ follows the first time $t_1$;

means for determining a third time $t_3$, wherein the vehicle driver starts to bring about compensation by actuation of the steering wheel at the third time $t_3$; and means for generating a signal which corresponds to the level of awareness of the vehicle driver by evaluation of a gradient of the steering-wheel angle ($\alpha$) during a time interval from the second time $t_2$ to the third time $t_3$.

16. An apparatus for detecting a level of awareness of a vehicle driver and a phase profile between a change in a steering angle ($\beta$) of at least one steerable wheel of a vehicle and a change in a steering-wheel angle ($\alpha$) of a steering wheel of the vehicle, the apparatus comprising:

at least one sensing device which detects a steering behavior of a vehicle;

mean for determining a first time $t_1$, wherein the change in the steering angle ($\beta$) begins at the first time $t_1$;

means for determining a second time $t_2$, wherein the change in the steering-wheel angle ($\alpha$) begins at the second time $t_2$ and the second time $t_2$ follows the first time $t_1$;

means for determining a third time $t_3$, wherein the vehicle driver starts to bring about compensation by actuation of the steering wheel at the third time $t_3$; and means for generating a signal which corresponds to the level of awareness by comparison of a gradient of the steering-wheel angle ($\alpha$) with a gradient of the steering angle ($\beta$).

* * * * *

UNITED STATES PATENT AND TRADEMARK OFFICE
CERTIFICATE OF CORRECTION

| | | |
|---|---|---|
| PATENT NO. | : 7,455,146 B2 | Page 1 of 1 |
| APPLICATION NO. | : 10/524351 | |
| DATED | : November 25, 2008 | |
| INVENTOR(S) | : Stefan Brosig et al. | |

It is certified that error appears in the above-identified patent and that said Letters Patent is hereby corrected as shown below:

Title Page, Item [73]

Assignee should read -- Volkswagen Aktiengesellschaft, Wolfsburg, Germany --

Signed and Sealed this

Fifteenth Day of February, 2011

David J. Kappos
*Director of the United States Patent and Trademark Office*